(12) United States Patent
Overaker et al.

(10) Patent No.: US 6,482,198 B2
(45) Date of Patent: Nov. 19, 2002

(54) HAND-HELD SURGICAL INSTRUMENTS WITH OMNI-CIRCUMFERENTIAL ACTUATION CAPABILITIES

(75) Inventors: Ronald F. Overaker, Durham; Cynthia A. Toth, Chapel Hill; Brian C. Dodge, Hillsborough; Brooks W. McCuen; Glenn J. Jaffe, both of Durham; Eric A. Postal, Raleigh; Sharon Fekrat, Durham, all of NC (US)

(73) Assignee: Duke University, Durham, NC (US)

( * ) Notice: Subject to any disclaimer, the term of this patent is extended or adjusted under 35 U.S.C. 154(b) by 8 days.

(21) Appl. No.: 09/837,555

(22) Filed: Apr. 19, 2001

(65) Prior Publication Data

US 2002/0156465 A1 Oct. 24, 2002

(51) Int. Cl.[7] .............................................. A61B 17/00
(52) U.S. Cl. .............................. 606/1; 606/210; 81/489
(58) Field of Search ........................ 606/1, 32, 106–108, 606/110, 205, 222, 228, 42, 161, 167, 210; 604/22; 81/489

(56) References Cited

U.S. PATENT DOCUMENTS

| | | | | | |
|---|---|---|---|---|---|
| 4,760,848 A | * | 8/1988 | Hasson | ........................ | 294/115 |
| 5,275,607 A | * | 1/1994 | Lo et al. | ........................ | 604/22 |
| 5,290,302 A | * | 3/1994 | Pericic | ........................ | 606/167 |
| 5,338,317 A | * | 8/1994 | Hasson et al. | ............... | 600/564 |
| 6,391,046 B1 | * | 5/2002 | Overaker et al. | ........... | 606/174 |

FOREIGN PATENT DOCUMENTS

DE   352 6821 A1 * 2/1987 ........... A61B/17/00

* cited by examiner

*Primary Examiner*—Teresa Walberg
*Assistant Examiner*—Thor Campbell
(74) *Attorney, Agent, or Firm*—Nixon & Vanderhye P.C.

(57) ABSTRACT

Hand-held instruments have an actuator assembly which may be employed to actuate a distally mounted tool by application of radial force about the entirety of the instrument circumference (i.e., is omni-actuatable). Most preferably, the actuator assembly includes a plurality of circumferentially spaced-apart generally L-shaped actuator levers defining respective arcuate bearing surfaces along exterior edge regions thereof, and a retaining ring which circumferentially bounds the actuator levers around the exterior edge regions thereof. The retaining ring most preferably defines an interior stationary arcuate guide surface in conformable mated relationship to the bearing surfaces of said actuator levers. Radial force applied to the proximally extending arm sections of said levers thereby responsively causes the bearing surfaces thereof to be slideably moved along the guide surface of said retaining ring so as to translate such radial force into longitudinal movements of an elongate actuation pin between retracted and extended positions thereof. By providing a tool which operatively coacts with the actuation pin, a surgeon may actuate the tool as needed by applying radial force at any point about the circumference of the actuator assembly.

32 Claims, 6 Drawing Sheets

HAND-HELD SURGICAL INSTRUMENTS WITH OMNI-CIRCUMFERENTIAL ACTUATION CAPABILITIES

FIELD OF THE INVENTION

The present invention relates generally to hand-held instruments and tools. In preferred forms, the present invention relates to hand-held surgical instruments, especially those usefully employed for ophthalmic surgical procedures.

BACKGROUND AND SUMMARY OF THE INVENTION

Ophthalmic surgical procedures require the use of miniaturized instruments such as, for example, forceps, scissors and the like in order to allow the surgeon to operate on and within a patient's eye. One well known instrument that is used for such ophthalmic surgical procedures is the so-called Sutherland-type instrument commercially available from Alcon Grieshaber. The Sutherland-type instrument has a pen-like handle and uses a lever as an actuator for actuating mechanically operable spring-loaded tools, such as forceps, scissors, knives and the like which are threaded or otherwise operably connected to the distal end of the handle.

Recently, improvements to such Sutherland-type instruments have been proposed in U.S. Pat. No. 5,634,918 (the entire content of which is expressly incorporated hereinto by reference). In general, the improvements proposed by the '918 Patent include providing a circumferentially arranged series of lever-like triggers which are pivotal in response to a radial force being applied thereto. Radially inward and outward pivotal movements of one trigger will, in turn, be converted respectively into rightward and leftward translation of the trigger retainer and is accompanied by like simultaneous movement of all the other triggers. Thus, any working tool attached operable to the trigger retainer will likewise translate rightward and leftward therewith.

Additional improvements in Sutherland-type instruments are disclosed in copending U.S. patent application Ser. No. 09/549,469 filed on Apr. 14, 2000, the entire content of which is expressly incorporated hereinto by reference, in which a radially flexible actuator band is seated in a generally V-shaped circumferential channel defined between a pair of rings, at least one of which is longitudinally moveable. In response to a radially compressive force. The actuator band will therefore be flexed radially inwardly so as to longitudinally move at least one of the slide rings, and hence a distally mounted tool operatively connected thereto.

The present invention is directed to further improvements in surgical instruments of the Sutherland-type. In this regard, the present invention broadly is directed to hand-held instruments which may be employed to actuate a distally mounted tool by application of radial force about the entirety of the instrument circumference (i.e., is omni-actuatable). In preferred forms, the present invention is embodied in hand-held instruments having a handle which includes an actuator assembly for actuating a tool, wherein the actuator assembly includes a plurality of circumferentially spaced-apart generally L-shaped actuator levers defining respective arcuate bearing surfaces along exterior edge regions thereof, and a retaining ring which circumferentially bounds the actuator levers around said exterior edge regions thereof. The retaining ring most preferably defines an interior stationary arcuate guide surface in conformable mated relationship to the bearing surfaces of said actuator levers.

In especially preferred embodiments, the actuation levers are one-piece structures which include a proximally extending manually actuable arm section, and a generally radially downwardly extending leg section. Bearing surfaces are defined along exterior edge regions of the levers at respective junctures between these arm and leg sections so as to cooperate with the conformably shaped guide surface of the retaining ring.

Most preferably the levers have proximally extending arm sections which are planar structural elements oriented coincidentally in respective radial planes emanating from the longitudinal axis of the device. These proximally extending arm sections thus define edge regions which establish generatrices of a curved surface (which may be convexly and/or concavely curved) in surrounding relationship to the device's longitudinal axis.

These as well as other aspects and advantages of the present invention will become more clear after careful consideration is given to the following detailed description of the preferred exemplary embodiments thereof.

BRIEF DESCRIPTION OF THE ACCOMPANYING DRAWINGS

Reference will hereinafter be made to the accompanying drawings, wherein like reference numerals throughout the various FIGURES denote like structural elements, and wherein.

DETAILED DESCRIPTION OF THE INVENTION

Figure 1:
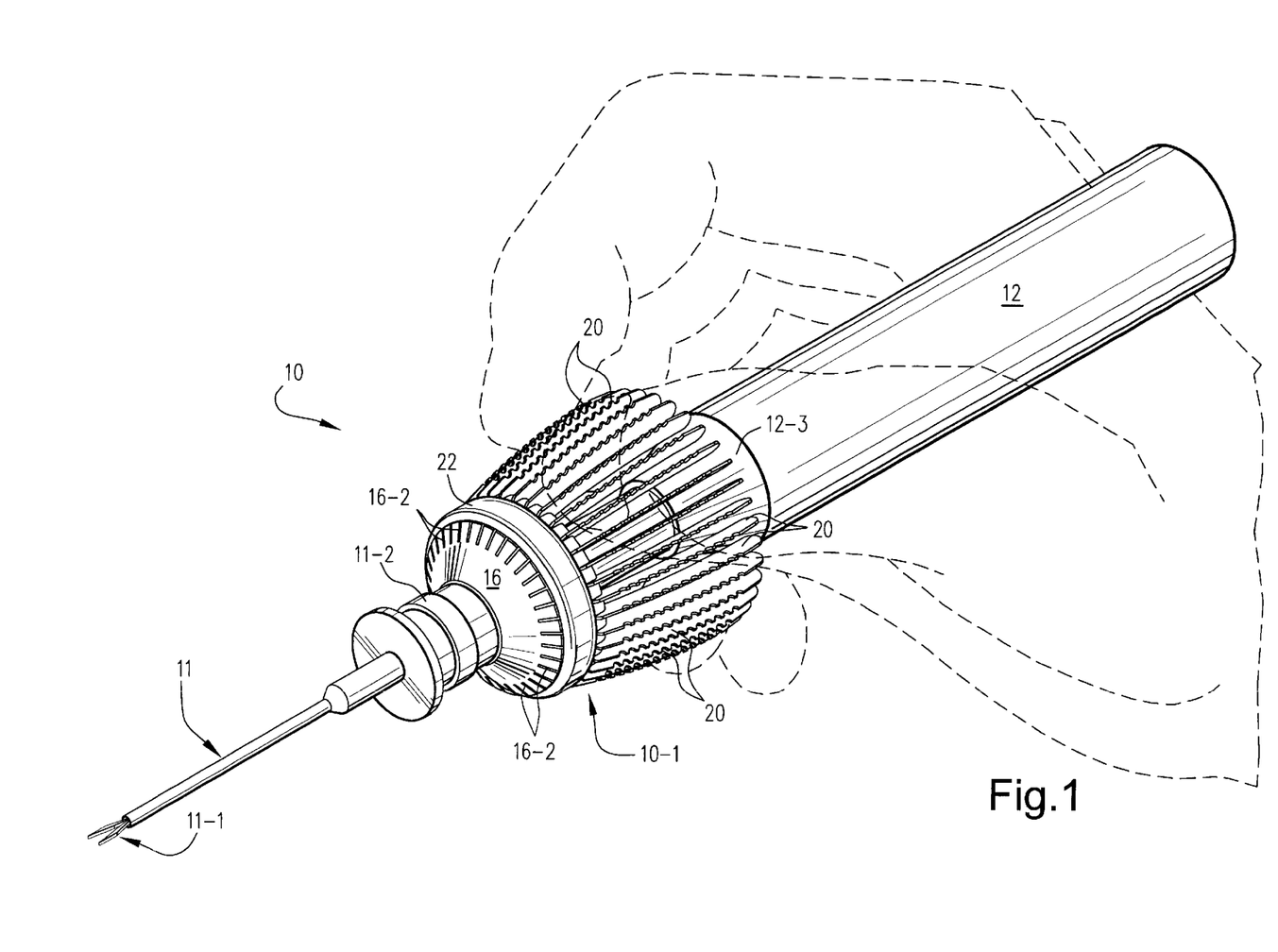
FIG. 1 is a perspective view of a hand-held surgical instrument in accordance with a presently preferred embodiment of the invention.

Accompanying FIG. 1 depicts an exemplary embodiment of a hand-held surgical instrument 10 according to the present invention. In this regard, the surgical instrument 10 includes an elongated handle 12 sized and configured to allow the instrument 10 to be handled manually by a surgeon during surgical procedures. The handle 12 includes a manually operated actuator assembly 10-1 which serves to actuate a tool 11 operatively attached to, and extending from, the distal end of the handle. The tool 11, for example, may be a miniature forceps 11-1 positioned at the distal-most end thereof which open and close in response to actuation of the actuator assembly 10-1 in a manner that will be described in greater detail below.

Figure 2:
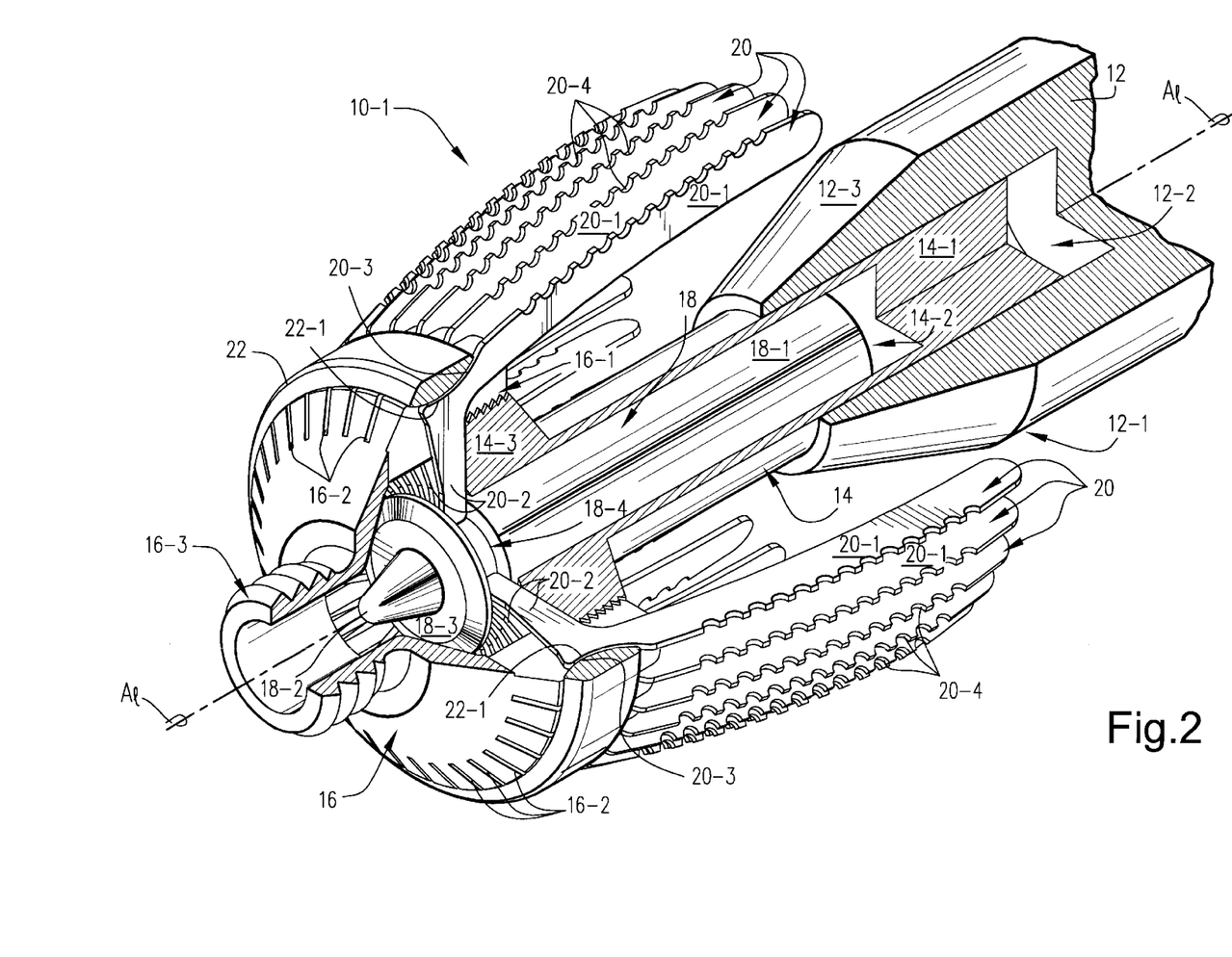
FIG. 2 is an enlarged perspective view of the actuator assembly employed in the surgical instrument of FIG. 1.

As is perhaps more clearly shown in accompanying FIG. 2, the distal end 12-1 of the handle 12 includes an axially elongate cylindrical recess 12-2 which receives a proximal correspondingly configured stem portion 14-1 of the actuation pin holder 14. The stem portion 14-1 of the actuation pin holder 14 is most preferably fixed immovably within the recess 12-2 by any convenient technique, for example, by press-fitting and/or adhesives, so that the actuation pin holder 14 is a rigid distal extension of the handle 12.

The distal end of the actuation pin holder 14 is provided with a circumferentially enlarged male head portion 14-3 which is threadably coupled to a threaded female recess portion 16-1 of the lever housing 16, the purpose and function of which will be described in greater detail below.

The actuation pin holder 14 also defines a distally open-ended, axially oriented, cylindrical hollow 14-2 which is sized so as to movably receive therewithin the proximal barrel portion 18-1 of the actuation pin 18. The barrel portion 18-1 is therefore capable of coaxially longitudinal sliding movements within the hollow 14-2 of the pin holder 14 so as to move axially between advanced and retracted conditions. In this regard, the structures are shown in accompanying FIG. 2 as being in their respective rest, or "normal" conditions. Thus, the "normal" condition for the actuation pin 18 is in its retracted condition as shown therein.

The distal end of the actuation pin 18 includes a generally conically shaped bearing nib 18-2 which distally projects from an axially transverse flange 18-3. An annular channel 18-4 is defined between the transverse flange 18-3 and the proximally disposed barrel portion 18-1 and receives the terminal end regions of each of the circumferentially spaced-apart actuation levers (a few of which are identified in FIG. 2 by reference numeral 20).

As shown, each of the actuation levers 20 is generally L-shaped and includes a proximally extending arm section 20-1 of substantially greater length as compared to the distal leg section 20-2. The levers 20 are most preferably one-piece structures and define an arcuately shaped bearing surface 20-3 along an outer edge region generally at the juncture of the arm and leg sections 20-1, 20-2.

The housing 16 defines a plurality of radially oriented slots corresponding in number to the number of actuation levers 20. The slots 16-2 are circumferentially spaced-apart from one another by an equal angular distance so that each receives therein a respective one of the actuation levers 20 generally at the juncture between the arm and leg sections 20-1 and 20-2. The levers 20 are thus also circumferentially spaced apart from one another about the central longitudinal axis $A_l$ (see FIG. 2) of the device 10 and thus the actuation pin 18 also. In such a manner, the arm sections 20-1 of each lever 20 extend proximally outwardly from the housing 16 and thus bridge the space between the housing 16 and the distal tapered end 12-3 of the handle 12 in coaxially circumferentially surrounding relationship to the actuation pin holder 14. These numerous exposed arm sections 20-1 of each actuation lever 20 thereby present the attending surgeon with a tactile sensation of a seemingly "solid" surface surrounding the central longitudinal axis of the device 10. Thus, the exposed proximally extending outer edge regions of the arm sections 20-1 will establish the generatrices of a curved surface which coaxially surrounds the longitudinal axis $A_l$ of the device 10 and essentially bridges the distance between the distal lever housing 16 and the proximal handle 12.

The actuation levers 20 are physically retained in each of their respective slots by an annular retaining ring 22 which bounds the housing 16 and the individual actuation levers 20 disposed in the slots 16-2. The retaining ring 22 defines an interior cross-sectionally arcuate stationary guide surface 22-1 which conformably mates with the bearing surface 20-3 of each of the actuation levers 20. Thus, the radii of curvature of each of the surfaces 22-1 and 20-3 are coincident with one another.

As will be observed particularly in FIGS. 1 and 2, the individual actuation levers 20 are most preferably relatively thin, planar structures which are oriented in the radial slots 16-2 of the housing 16 so as to be disposed coincident with radial planes from the central axis $A_l$. The exposed outer proximal edge regions of each of the levers 20 may thus be provided with serrations 20-4 so as to promote a more rough feel to the attending surgeon. Other means may also be employed in order to improve the tactile sensation and/or feel of the levers 20, such as, for example coating at least the external exposed edges of the levers with a friction material (e.g., an elastomeric material) or the like.

Figure 3:
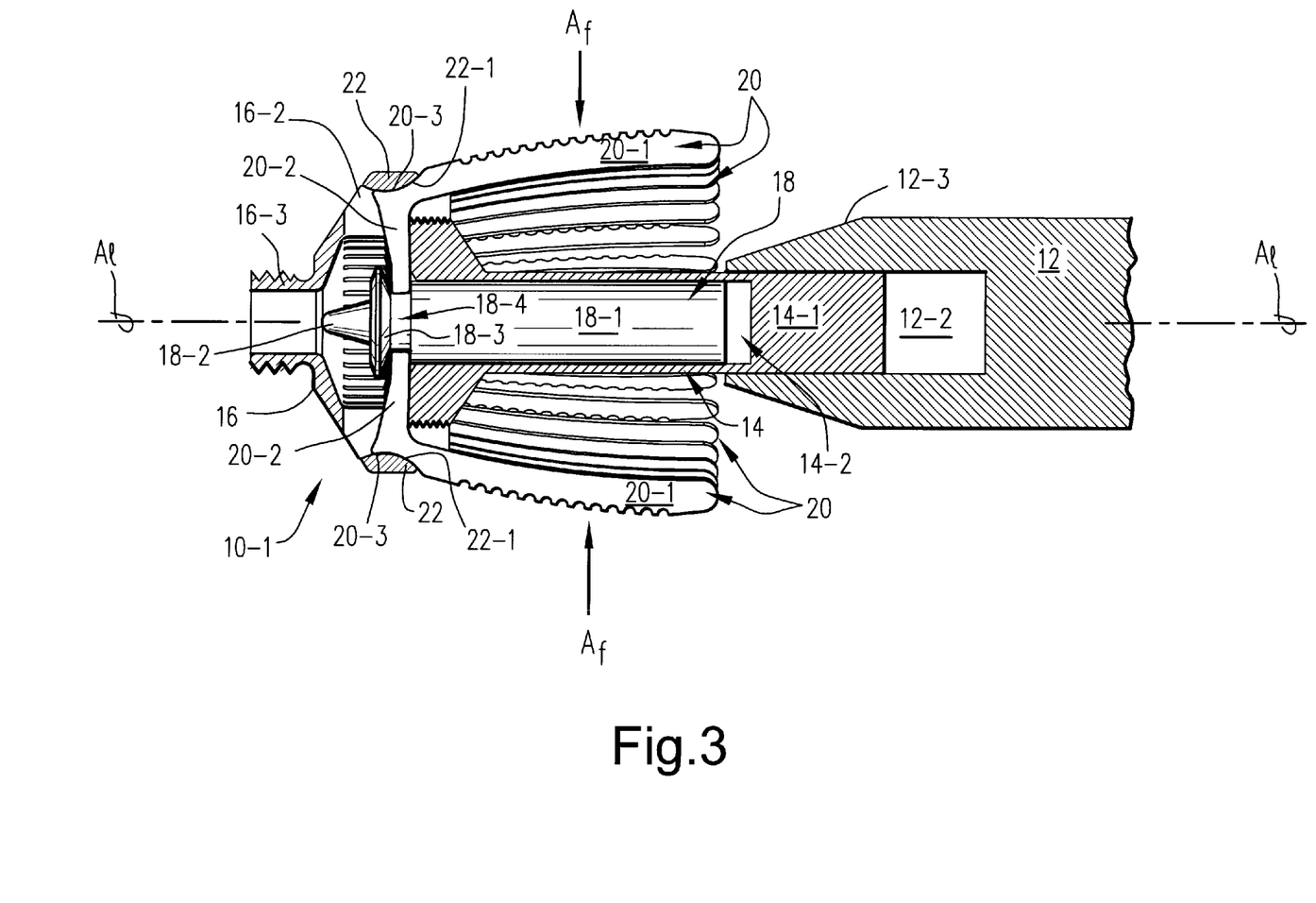
FIGS. 3 and 4 each depict a cross-sectional elevational view of the actuator assembly of the present invention in rest and operative conditions thereof, respectively.
Figure 4:
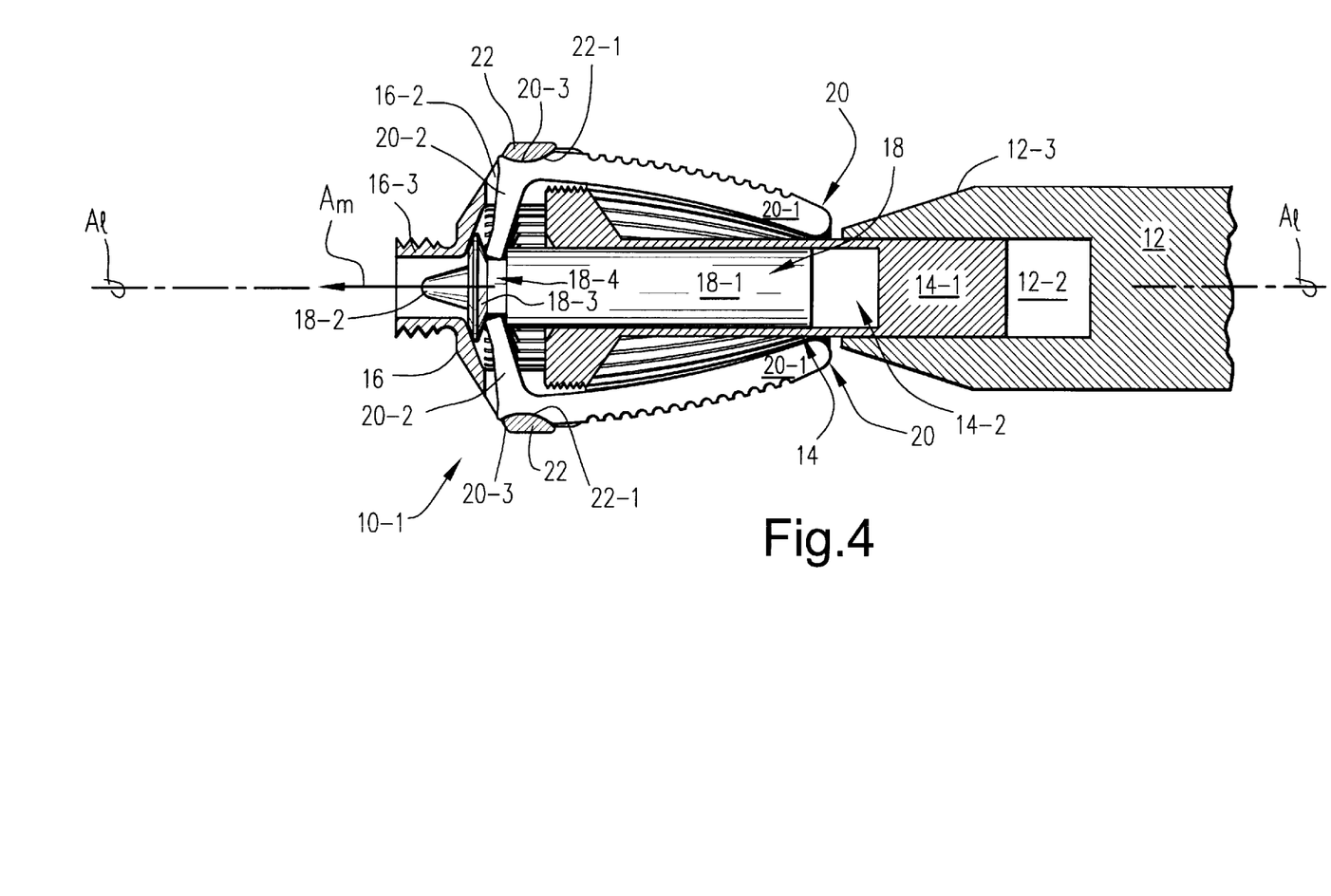

The operation of the actuator assembly 10-1 employed in the hand-held surgical device 10 in accordance with the present invention is depicted generally in accompanying FIGS. 3 and 4. In this regard, the proximal end 11-2 of the tool 11 (see FIG. 1) may be threadably and removeably connected to the threaded nipple 16-3 coaxially extending distally from the housing 16. Although not shown, the tool 11 will conventionally have an actuator rod which extends through the nipple 16-3 proximally into operative engagement with the bearing nib 18-2. Moreover, the tool 11 is conventionally provided with a spring element which urges the actuation rod thereof into contact with the activation nib 18-2. Thus, the force of the tool's spring element will cause the actuation pin 18 to be displaced proximally within the holder 14 so that it assumes its "normal" or rest condition as shown in FIG. 3.

Upon application of a radially inwardly directed force (as noted by the arrows $A_f$ in FIG. 3), the lever arms 20-1 are caused to move collectively toward the holder 14 (that is, to be moved to a position closer to the central axis $A_l$ of the device 10). More specifically, the bearing surfaces 20-3 of the levers 20 are caused to slide along the cross-sectionally arcuate guide surface 22-1 of the retainer ring 22 so that as to cause the radially inwardly directed lever leg 20-2 to be moved generally pivotally from its rest condition as shown in FIG. 3 to its active condition as shown in FIG. 4. As will be observed, since the terminal ends of each of the legs 20-2 are received within the annular channel 18-4 of the actuation pin 18, such movement (or "throw") of the lever legs 20-2 will translate in coaxial linear movement of the actuator pin 18 (and hence its distally extending actuation nib 18-2) from its rest position as shown in FIG. 3 to its actuation condition in the direction of arrow $A_m$ as shown in FIG. 4. Thus, the nib 18-2 will push the tool's actuation rod (not shown) distally against the bias force of the tool's spring element (also not shown) to cause actuation of the working elements of the tool 11, such as the miniature forceps 11-1 as depicted in FIG. 1.

It should be noted here that, although the tool 11 is in and or itself conventional and of the type that may be employed generally in combination with Sutherland-type instruments—that is, will have its own self-contained spring element—the surgical devices 10 in accordance with this invention could alternatively (or additionally) be provided with a spring element. For example, a spring element could be positioned within the hollow 14-2 of the holder 14 and exert an appropriate bias force on the actuation pin 18 as may be required or desired.

Figure 5A:
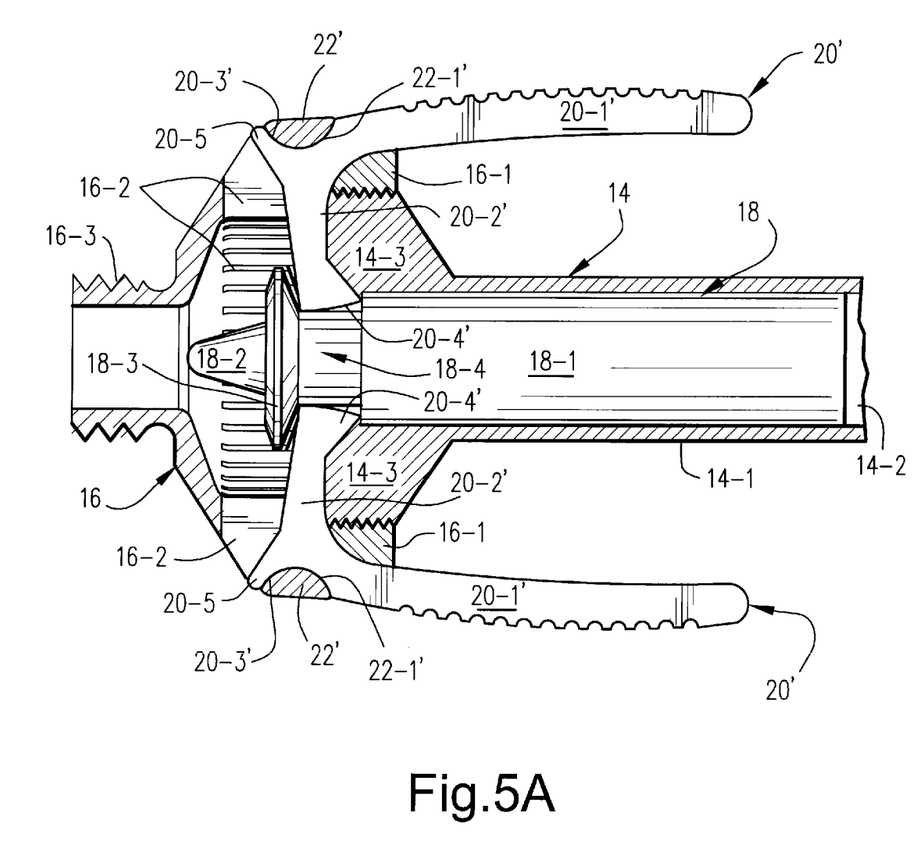
FIGS. 5A and 5B depict an alternative embodiments of the actuating levers that may be employed in the present invention.
Figure 5B:
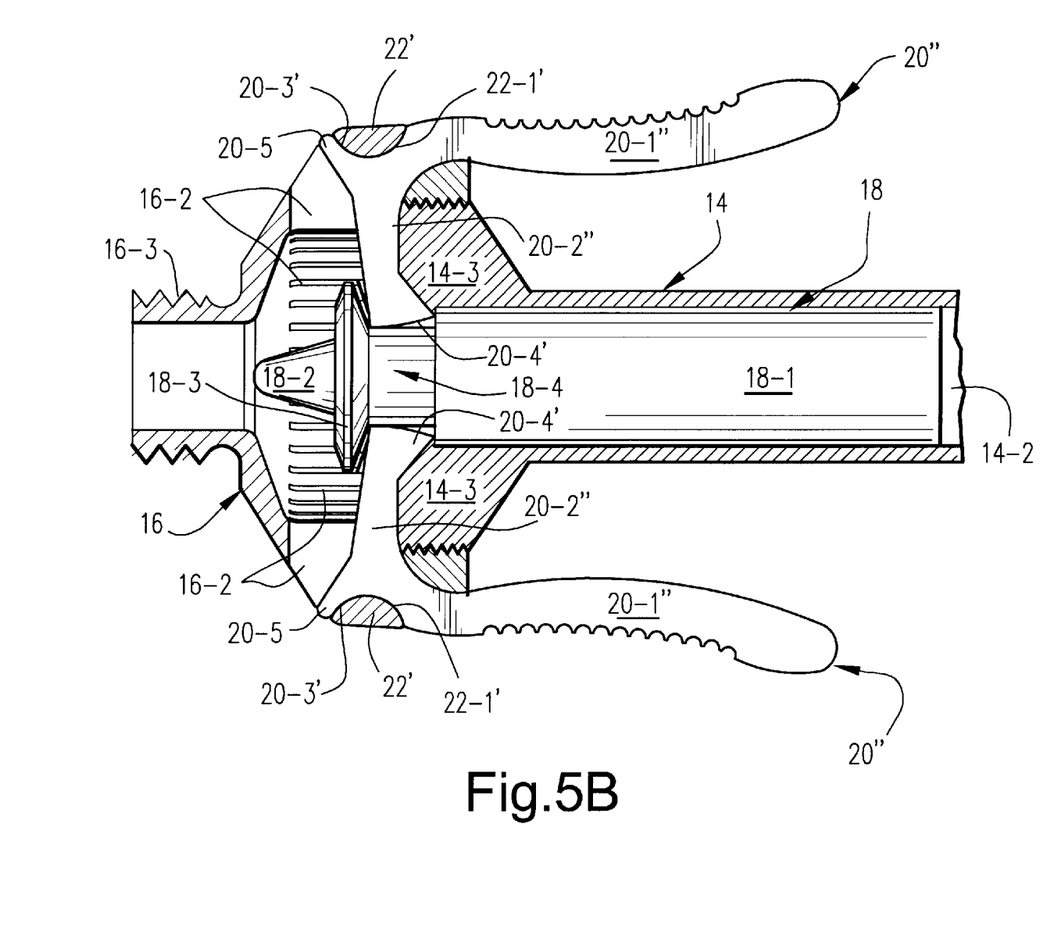

Accompanying FIGS. 5A and 5B depict alternative embodiments of the actuator assembly 10-1 that may be employed in the devices of the present invention. In this regard, each of the actuator assemblies 10-1' and 10-1" shown in FIGS. 5A and 5B, respectively, is generally identical to the actuator assembly 10-1, with the principal exceptions being the configurations of the levers 20 and the retaining ring 22. Thus, identical structural elements among the various embodiments are noted by the same reference numerals.

By way of example, the embodiment depicted in FIG. 5A includes actuation levers 20' which define a generally semi-circular bearing surface 20-3' provided generally at the juncture between the proximally extending lever arm sections 20-1' and the downwardly radially projecting leg sections 20-2'. This bearing surface 20-3' therefore bears against, and cooperates with, a semi-circularly shaped guide surface 22-1' defined in cross-section by the retaining ring 22'. A retaining lip 20-5 is also provided as an extension of sorts of the bearing surface 20-3' and therefore projects somewhat distally around the guide surface 22-1' so as to assist in the sliding movement of the bearing surface 20-3' against the stationary guide surface 22-1'.

The terminal ends of the lever leg sections 20-2' terminate in a slightly arcuate terminal edge 20-4' which is received within the recessed channel 18-4 of the actuation pin 18. The center of the arcuate terminal edge 20-4' is coincident with centers of the semi-circular bearing surface 20-3' and guide surface 22-1', capturing the levers 20' between them. The arcuate edges 20-4' of the leg sections 20-2' thereby help to ensure relatively smooth pivoting of the levers 20-1' around the coincident centers of the arcs defined by the surfaces 20-3', 22-1' and 20-4' and thus relatively smooth movements of the actuation pin 18. The coincident centers of the arcs defined by surfaces 20-3', 22-1' and 20-4' may lie outside the major diameter of the handle.

It will also be observed that the leg sections 20-2' project downwardly and somewhat proximally as compared to the leg sections 20-2 discussed previously. Thus, instead of the arm and leg sections 20-1 and 20-2, respectively forming a substantially right (or minimally obtuse) angle therebetween, the arm and leg sections 20-1' and 20'-2' form a somewhat acute angle therebetween.

The levers 20" shown in FIG. 5B are substantially identical to the levers 20' shown in FIG. 5A except for the curvature of the arm sections 20-1" thereof. In this regard, it will be observed that, whereas the proximally extending arm sections 20-1' of the levers 20' shown in FIG. 5A have a slight convex curvature, the arm sections 20-1" have a slight concave curvature. Of course, the levers that may be employed in the practice of this invention may have virtually any geometric configuration and/or curvature combination (including levers having respective sections of convex and concave curvatures) as may be desired by an individual physician's personal preference. Thus, for example, instead of having any curvature (concave and/or convex), the levers may define a linear edge which is substantially parallel or even somewhat angularly disposed relative to the longitudinal axis $A_l$.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A tool actuator assembly for a hand-held surgical device comprising:
   a plurality of circumferentially spaced-apart generally L-shaped actuator levers having arcuate bearing surfaces along exterior edge regions thereof; and
   a retaining ring which circumferentially bounds said actuator levers around said exterior edge regions thereof so as to hold said actuator levers in a fixed, spaced relationship to each other, wherein
   said retaining ring defines an interior stationary arcuate guide surface in conformable mated relationship to said bearing surfaces of said actuator levers.

2. The tool actuator assembly of claim 1, wherein said actuation levers are one-piece structures which include (i) a proximally extending manually actuable arm section, and (ii) a generally radially inwardly extending leg section, and wherein said bearing surfaces are defined along said exterior edge regions at respective junctures generally between said arm and leg sections.

3. The tool actuator assembly of claim 2, wherein said actuation levers are substantially planar structures which are oriented in respective planes radiating from a longitudinal axis of the hand-held surgical device.

4. The tool actuator assembly of claim 3, wherein the actuation levers include serrations along proximal outer edge regions thereof.

5. The tool actuator assembly of claim 3, which further comprises a lever housing which defines a plurality of circumferentially spaced-apart radial slots for accepting respective ones of the levers.

6. The tool actuator assembly of claim 5, wherein the retaining ring circumferentially bounds said lever housing so as to retain the levers in said slots thereof.

7. The tool actuator assembly of claim 1, which further comprises an actuation pin reciprocally moveable longitudinally between retracted and extended positions.

8. The tool actuator assembly of claim 7, wherein said levers include generally inwardly radially extending leg sections having terminal end regions which are operatively connected to said actuation pin.

9. The tool actuator assembly of claim 8, wherein said actuator pin includes a proximal cylindrical barrel portion, a distally projecting bearing nib, and an annular recessed channel defined between said barrel portion and said nib, and wherein said terminal end regions of said leg sections are operably received within said recessed channel.

10. The tool actuator assembly of claim 9, wherein said terminal end regions of said leg sections define arcuate edges having radius centers coincident with said arcuate guide and bearing surfaces.

11. A hand-held surgical device comprising:
    a proximal elongate handle which defines a longitudinal axis of the device;
    a distal lever housing; and
    a plurality of circumferentially spaced-apart levers operatively associated with said housing and having proximally extending arm sections, wherein
    said proximally extending arm sections are planar structural elements which are oriented coincidentally in respective radial planes emanating from the longitudinal axis, and wherein
    said proximally extending arm sections define edge regions which establish generatrices of a curved surface which surrounds said longitudinal axis.

12. The device of claim 11, wherein said edge regions establish generatrices of a curved convex surface.

13. The device of claim 11, wherein said edge regions establish generatrices of a curved concave surface.

14. The device of claim 11, wherein said proximal edge regions include serrations.

15. The device of claim 11, wherein said levers are generally L-shaped planar, one-piece structural elements having inwardly oriented leg regions extending from said proximally extending arm regions.

16. The device of claim 11, wherein said lever housing has a distally extending nipple for being operatively coupled with a surgical tool.

17. The device of claim 11, further comprising:

an actuation pin holder connected between said handle and said lever housing, and defining a distally open-ended, axially oriented, cylindrical hollow, and an actuation pin having a proximal cylindrical barrel portion received within said hollow of said holder for reciprocal longitudinal movements therewithin.

18. The device of claim 17, wherein said levers include leg sections extending radially inwardly toward, and being operatively connected to, said actuation pin.

19. The device of claim 18, wherein said actuator pin includes a distally projecting bearing nib, and an annular recessed channel defined between said barrel portion and said nib, and wherein said leg sections of said levers have terminal end regions which are operably received within said annular recessed channel.

20. The device of claim 19, wherein said terminal end regions of said leg sections include arcuate edges.

21. A hand-held surgical device comprising:

a proximal handle;

a distal lever housing;

an actuator pin holder extending between and connecting said proximal handle and said distal lever housing, said holder defining a distally open-ended, axially oriented, cylindrical hollow;

an actuation pin having a proximal cylindrical barrel portion received within said hollow of said holder for reciprocal longitudinal movements therewithin between retracted and extended positions;

a plurality of circumferentially spaced apart levers having (i) proximally extending arm sections which surround said holder in radially spaced relationship thereto, (ii) radially inwardly extending leg sections operatively coupled to said actuation pin, and (iii) arcuate bearing surfaces defined along exterior edge regions at a juncture between said arm and leg sections; and a retaining ring which circumferentially bounds said actuator levers around said exterior edge regions thereof so as to retain said levers in operative association with said lever housing, wherein said retaining ring defines an interior stationary arcuate guide surface in conformable mated relationship to said bearing surfaces of said actuator levers, and wherein radial force applied to said proximally extending arm sections of said levers causes said bearing surfaces thereof to be slideably moved along said guide surface of said retaining ring so as to translate such radial force into longitudinal movements of said actuation pin between said retracted and extended positions thereof.

22. The device of claim 21, wherein said levers are generally L-shaped one-piece planar structures.

23. The device of claim 22, wherein said levers are oriented coincidentally in respective radial planes emanating from a longitudinal axis of the device such that said proximally extending arm sections define edge regions which establish generatrices of a curved surface which surrounds said longitudinal axis.

24. The device of claim 23, wherein said edge regions establish generatrices of a curved convex surface.

25. The device of claim 23, wherein said edge regions establish generatrices of a curved concave surface.

26. The device of claim 23, wherein said proximal edge regions include serrations.

27. The device of claim 21, wherein said actuator pin includes a distally projecting bearing nib, and an annular recessed channel defined between said barrel portion and said nib, and wherein said leg sections of said levers have terminal end regions which are operably received within said annular recessed channel.

28. The device of claim 27, wherein said terminal end regions of said leg sections include arcuate edges.

29. The device of claim 28, arcuate edges have radius centers which coincident with said arcuate guide and bearing surfaces.

30. The device of claim 21, wherein said holder includes a distal male head portion which is threadably coupled to a proximal recessed threaded female portion of said housing.

31. The device of claim 21, wherein said handle includes a distal tapered region.

32. The device of claim 21, wherein said handle includes a cylindrical handle recess, and wherein said holder has a proximal cylindrical stem which is immovably fixed within said handle recess.

* * * * *

UNITED STATES PATENT AND TRADEMARK OFFICE
CERTIFICATE OF CORRECTION

PATENT NO. : 6,482,198 B1
DATED : November 19, 2002
INVENTOR(S) : Overaker et al.

It is certified that error appears in the above-identified patent and that said Letters Patent is hereby corrected as shown below:

<u>Title page,</u>
Item [75], Inventors, change "Eric A. Postal" to -- Eric A. Postel --.

Signed and Sealed this

Eighteenth Day of March, 2003

JAMES E. ROGAN
*Director of the United States Patent and Trademark Office*